(12) United States Patent
Biffi et al.

(10) Patent No.: US 9,233,936 B2
(45) Date of Patent: Jan. 12, 2016

(54) PROCESS FOR THE PREPARATION OF BOSENTAN

(75) Inventors: Giancarlo Biffi, Milan (IT); Lazzaro Feliciani, Milan (IT); Enrico Viscardi, Milan (IT)

(73) Assignee: SIFAVITOR S.R.L., Milano (MI) (IT)

( * ) Notice: Subject to any disclaimer, the term of this patent is extended or adjusted under 35 U.S.C. 154(b) by 554 days.

(21) Appl. No.: 13/254,548

(22) PCT Filed: Mar. 3, 2010

(86) PCT No.: PCT/IB2010/000431
§ 371 (c)(1),
(2), (4) Date: Oct. 3, 2011

(87) PCT Pub. No.: WO2010/103362
PCT Pub. Date: Sep. 16, 2010

(65) Prior Publication Data
US 2012/0041200 A1    Feb. 16, 2012

(30) Foreign Application Priority Data
Mar. 11, 2009    (IT) .............................. MI2009A0361

(51) Int. Cl.
*C07D 239/52*    (2006.01)
(52) U.S. Cl.
CPC .................... *C07D 239/52* (2013.01)
(58) Field of Classification Search
CPC .................................................... C07D 239/52
See application file for complete search history.

(56) References Cited

U.S. PATENT DOCUMENTS

| 4,920,230 A * | 4/1990 | Kato ............................. 546/290 |
| 5,292,740 A * | 3/1994 | Burri et al. .................... 514/256 |

FOREIGN PATENT DOCUMENTS

| EP | 0526708 | | 2/1993 |
| GB | WO 2009/004374 | * | 1/2009 |
| IN | WO 2009/095933 | * | 8/2009 |
| WO | WO 2009/004374 | | 1/2009 |
| WO | WO 2009/093127 | | 7/2009 |
| WO | WO 2009/095933 | | 8/2009 |
| WO | WO 2010/032261 | | 3/2010 |

OTHER PUBLICATIONS

International Search Report for PCT/IB2010/000431 mailed Aug. 27, 2010.
Written Opinion for PCT/IB 2010/000431 mailed Aug. 27, 2010.

* cited by examiner

*Primary Examiner* — Valerie Rodriguez-Garcia
(74) *Attorney, Agent, or Firm* — Nixon & Vanderhye P.C.

(57) ABSTRACT

The invention concerns a new process for the preparation of bosentan or bosentan monohydrate by reaction of compound of Formula II with ethylene glycol in the presence of potassium bases and the potassium salt of bosentan.

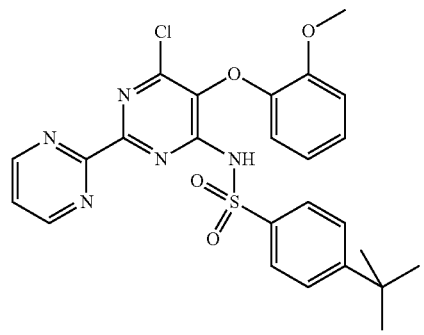

(II)

7 Claims, No Drawings

PROCESS FOR THE PREPARATION OF BOSENTAN

This application is the U.S. national phase of International Application No. PCT/IB2010/000431 filed 3 Mar. 2010 which designated the U.S. and claims priority to MI2009A000361 filed 11 Mar. 2009, the entire contents of each of which are hereby incorporated by reference.

SUMMARY OF THE INVENTION

The present invention concerns a new process for the preparation of bosentan and a new salt thereof. In particular the invention concerns a process that can be industrially implemented for the preparation of bosentan or bosentan monohydrate which allows the compound to be obtained with a high purity, in a few easy reaction steps and with excellent yields.

PRIOR ART

The term bosentan is the international non-proprietary name of the compound 4-tert-butyl-N-[6-(2-hydroxyethoxy)-5-(2-methoxy-phenoxy)-[2,2']bipyrimidinyl-4-yl]-benzenesulfonamide which is a receptor antagonist for endothelin-1 used for the treatment of patients suffering from pulmonary hypertension.

Some syntheses for the preparation of bosentan are known.

EP patent 526708 describes the synthesis of bosentan by reaction of the compound 4-tert-butyl-N-[6-chloro-5-(2-methoxy-phenoxy)-[2,2]bipyrimidinyl-4-yl]-benzenesulfonamide with 2-hydroxy sodium ethanolate. As reported also by the subsequent patent EP 1254121, said synthesis leads to the formation of abundant reaction by-products such as the compound dimer, i.e. the product of the reaction between two molecules of sulfonamidic derivative and one molecule of ethylene glycol. Said by-product is difficult and costly to separate.

To remedy said drawback, the patent EP 1254121 proposes a synthesis of the bosentan which comprises reacting the above-mentioned benzenesulfonamidic derivative with the 2-hydroxy sodium ethanolate having the free hydroxyl protected by a tert-butyl group, i.e. with the compound of formula

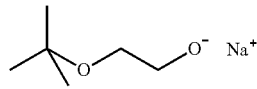

To obtain bosentan, the protected intermediate that has formed must then be de-protected, for example by transformation of the tert-butyl protecting group into the formyl derivative and subsequent removal of the formyl group with a base.

It is apparent that although this process overcomes the drawbacks of the patent EP 526708, i.e. it avoids the formation of dimer, it involves at least two further reaction steps. From an industrial point of view, two additional steps obviously increase the cost of the process, therefore making it uneconomical.

Furthermore, the applicant has ascertained that, contrary to what is described in the patent EP 1254121, operating in the reaction conditions indicated, the protected intermediate cannot be isolated by precipitation and the final yield is below the figure declared in said patent.

Moreover, the applicant has observed that isolation of the sodium salt of the bosentan obtained according to the process of the patent EP 526708 also involves considerable technical difficulties.

WO2009/004374 describes a process for the preparation of bosentan which comprises adding the 4-tert-butyl-N-[6-chloro-5-(2-methoxy-phenoxy)-[2,2']bipyrimidinyl-4-yl]-benzenesulfonamide to a mixture of ethylene glycol and hydroxide ions, in particular sodium, potassium or lithium hydroxides.

DISCLOSURE OF THE INVENTION

The present invention remedies the drawbacks of the prior art by means of a simple economic process which involves only a few reaction steps and produces bosentan with excellent yields and high purity.

It has been found, unexpectedly and surprisingly, that it is possible to obtain bosentan, with excellent yields and without the formation of undesired by-products, by reacting the 4-tert-butyl-N-[6-chloro-5-(2-methoxy-phenoxy)-[2,2']bipyrimidinyl-4-yl]-benzenesulfonamide with ethylene glycol, non-protected, in the presence of particular bases. Pre-selection of the bases, as will be clarified below, is not random but performed in order to obtain bosentan with excellent yields and good purity, a result which cannot be obtained with the use of other bases, for example by using hydroxides.

Thus, according to one of its embodiments, the invention concerns a process for preparation of the bosentan of formula (I)

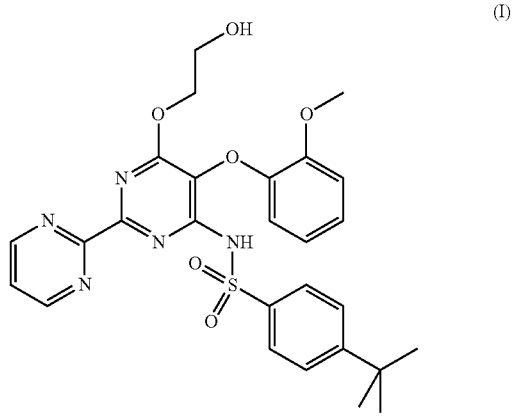 [SMILES: COc1ccccc1Oc1c(NS(=O)(=O)c2ccc(C(C)(C)C)cc2)nc(-c2ncccn2)nc1OCCO]

or a salt or a hydrate thereof, which comprises reacting 4-tert-butyl-N-[6-chloro-5-(2-methoxy-phenoxy)-[2,2']bipyrimidinyl-4-yl]-benzenesulfonamide of formula (II)

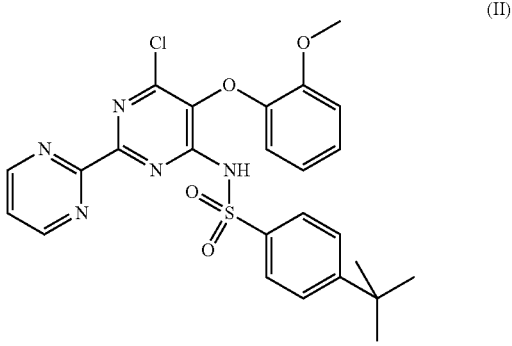 [SMILES: COc1ccccc1Oc1c(Cl)nc(-c2ncccn2)nc1NS(=O)(=O)c1ccc(C(C)(C)C)cc1]

with ethylene glycol, in the presence of a base chosen from potassium phosphate tribasic ($K_3PO_4$), potassium carbonate ($K_2CO_3$), potassium hydride (KH) and a secondary or tertiary potassium alcoholate, to give the potassium salt of bosentan of formula (III)

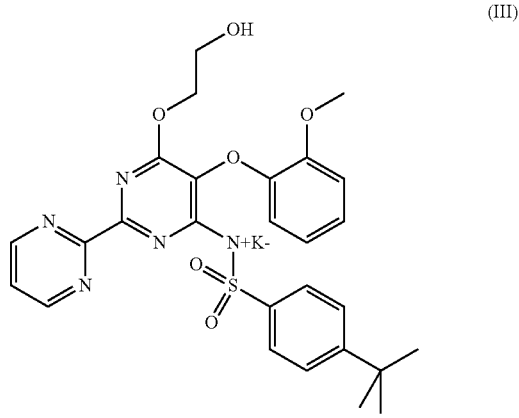

(III)

"Secondary or tertiary potassium alcoholate" means, according to the present invention, an Alk-OK base in which Alk is an alkyl containing 3 to 5 atoms of secondary or tertiary carbon. Suitable alcoholates are, for example, potassium isopropylate, potassium isobutylate, potassium tert-butylate and potassium tert-amylate.

The choice of the above bases is critical for preparation of the bosentan with good yields and makes easy processing on an industrial scale possible.

According to a particularly preferred embodiment, the base used is potassium phosphate tribasic.

Another preferred base of the invention is potassium tert-butylate but said base is more costly than the other bases indicated and furthermore is less easy to handle at industrial level.

According to a preferred embodiment, the reaction is performed in an inert atmosphere, for example in a nitrogen atmosphere, at a temperature between 80° C. and 150° C., preferably between 90° C. and 130° C., advantageously between 100° C. and 120° C., for example around 110° C., until completion of the reaction.

The quantities of ethylene glycol and base are not critical, on condition that they are in excess with respect to the starting compound (II).

Normally the reaction is complete after 12-36 hours; a person skilled in the art is able to ascertain the progress thereof by means of the conventional methods.

Once the reaction is complete, the mixture is advantageously diluted with water and cooled to produce the potassium salt of the bosentan of formula (III).

According to a preferred embodiment, the compound of formula (III) is purified by crystallisation, for example by crystallisation in ethylene glycol, advantageously in an inert atmosphere, in the presence of a base chosen from potassium phosphate tribasic ($K_3PO_4$) and potassium carbonate ($K_2CO_3$). The potassium phosphate tribasic is a preferred base. Examples of reaction and crystallisation are reported in the experimental section of the present disclosure.

The potassium salt of the bosentan of formula (III) is a new compound and constitutes a further subject-matter of the present invention, likewise its use for the preparation of bosentan and bosentan monohydrate is also a subject-matter of the invention.

It has been unexpectedly found that said potassium salt precipitates better and can be more easily filtered than the sodium salt of the bosentan and for this reason its purification is facilitated.

In order to obtain the bosentan, the salt of formula (III) can be treated with an acid, mineral or organic, for example hydrochloric acid, in a solvent or in a mixture of appropriate solvents.

According to a preferred embodiment of the present invention, the potassium salt of formula (III) is recovered in a biphasic mixture of water and a solvent immiscible with the water such as methyl isobutyl ketone, toluene or isopropyl acetate, advantageously but not necessarily in an inert atmosphere; hydrochloric acid is then added, heating until the biphasic system is limpid. After separation of the phases, the bosentan monohydrate precipitates by cooling. In this reaction, the water/methyl isobutyl ketone mixture is the preferred mixture.

If desired or necessary, the compound obtained can be purified by crystallisation. By way of example, the bosentan monohydrate can be prepared by crystallisation from ethanol and water, as reported in the experimental section of the present disclosure.

The starting compound of formula (II) is known and can be prepared according to the known methods described in the art. An example of said preparation is provided for purely illustrative purposes in the following experimental section.

In addition to better illustrating the invention, naturally in a non-limiting manner, the experimental section furthermore includes comparative examples which demonstrate the improved effectiveness of the bases used according to the invention with respect to the bases described in the prior art.

EXPERIMENTAL SECTION

Example 1

Preparation of the compound of formula (II) 4-tert-butyl-N-[6-chloro-5-(2-methoxy-phenoxy)-[2,2'] bipyrimidinyl-4-yl]-benzenesulfonamide 44 g (0.21 moles) of 4-tert-butyl-benzenesulfonamide, 72 g (0.21 moles) of 4,6-dichloro-5-(2-methoxy-phenoxy)-[2, 2']bipyrimidine and 0.7 g of tetrabutylammonium bromide are added to a suspension of 35 g (0.25 moles) of potassium carbonate in 720 ml of methyl isobutyl ketone (MIBK), kept in an inert atmosphere (nitrogen). Once the addition is complete, the suspension is heated to reflux, operating so as to azeotropically remove the water that forms during the reaction. The reaction is kept at reflux for 5 hours. Once the reaction is complete, the suspension is cooled to 50° C. and diluted with 0.2 liters of water. Hydrochloric acid 35% is then added until obtaining a pH between 2.0 and 3.0. The suspension is cooled to 5° C./10° C. and the product is left to crystallise for 10 hours. The suspension is filtered and 120 g in wet form of the title compound are obtained equal to 100 g in dry form (0.19 moles) (yield 92%; purity 99.6% HPLC).

Example 2

Preparation of the compound of formula (III) with potassium phosphate tribasic potassium salt of 4-tert-butyl-N-[6-(2-hydroxy-ethoxy)-5-(2-methoxy-phenoxy)-[2,2']bipyrimidinyl-4-yl]-benzenesulfonamide The solid from example 1 is added to a solution of 161 g (0.76 moles) of potassium phosphate tribasic in 1.5 liters of ethylene glycol, kept in an inert atmosphere (nitrogen). Once the addition is complete, the suspension is heated to 110° C. and maintained for 24 hours. During the reaction, a complete solution is obtained. Once the reaction is complete, the solution is cooled to 90° C. and diluted with 1.5 liters of water. The solution is cooled to 15° C. and the product is left to crystallise for 5 hours. The suspension is filtered and 120 g in wet form of the title compound are obtained equal to 100 g in dry form (0.17 moles) (yield 89%; purity 98.8% HPLC).

Example 3

Purification of the compound of formula (III) potassium salt of 4-tert-butyl-N-[6-(2-hydroxy-ethoxy)-5-(2-methoxy-phenoxy)-[2,2']bipyrimidinyl-4-yl]-benzenesulfonamide The solid from example 2 is placed in 1.0 liters of ethylene glycol in an inert atmosphere (nitrogen). 36 g (0.17 moles) of potassium phosphate tribasic are added. The suspension is heated until totally dissolved. It is then cooled to 90° C. and diluted with 1.0 liters of water. The solution is cooled to 15° C. and the product is left to crystallise for 5 hours. The suspension is filtered and 105 g in wet form of the purified title compound are obtained equal to 95 g in dry form (0.16 moles) (yield 95%; purity 99.6% HPLC).

Example 4

Preparation of the compound of formula (I) (bosentan monohydrate) 4-tert-butyl-N-[6-(2-hydroxy-ethoxy)-5-(2-methoxy-phenoxy)-[2,2']bipyrimidinyl-4-yl]-benzenesulfonamide monohydrate The solid from example 3 is placed in a mixture consisting of 0.57 liters of methyl isobutyl ketone and 0.2 liters of water in an inert atmosphere (nitrogen). 17 g (0.16 moles) of hydrochloric acid 35% are added to the suspension obtained. The suspension is heated to 75° C. so that the 2 phases are perfectly limpid. The aqueous phase is decanted. The solution is cooled to 15° C. and the product is left to crystallise for 12 hours. The suspension is filtered. The wet solid obtained is placed in 0.4 liters of absolute ethanol in an inert atmosphere (nitrogen). The suspension is heated to reflux in order to obtain complete solution. It is diluted with 0.4 liters of water, always maintaining the reflux. The solution is cooled to 15° C. and the product is left to crystallise for 2 hours. The suspension is filtered and the bosentan monohydrate thus obtained is dried at 60° C. under a vacuum (purity 99.9% HPLC).

Example 5

Preparation of the compound of formula (III) with potassium carbonate potassium salt of 4-tert-butyl-N-[6-(2-hydroxy-ethoxy)-5-(2-methoxy-phenoxy)-[2,2']bipyrimidinyl-4-yl]-benzenesulfonamide 20 g (38 mmoles) of 4-tert-butyl-N-[6-chloro-5-(2-methoxy-phenoxy)-[2,2']bipyrimidinyl-4-yl]-benzenesulfonamide are added to a solution of 26 g (188 mmoles) of potassium carbonate in 300 ml of ethylene glycol, kept in an inert atmosphere (nitrogen). Once the addition is complete, the suspension is heated to 110° C. and maintained for 24 hours. During the reaction, a complete solution is obtained. Once the reaction is complete, the solution is cooled to 90° C. and diluted with 300 ml of water. The solution is cooled to 15° C. and the product is left to crystallise for 5 hours. The suspension is filtered. 20 g in wet form equal to 17 g in dry form (29 mmoles) are obtained; yield approximately 76%.

Example 6

Preparation of the compound of formula III with potassium tert-butylate potassium salt of 4-tert-butyl-N-[6-(2-hydroxy-ethoxy)-5-(2-methoxy-phenoxy)-[2,2']bipyrimidinyl-4-yl]-benzenesulfonamide 20 g (38 mmoles) of 4-tert-butyl-N-[6-chloro-5-(2-methoxy-phenoxy)-[2,2']bipyrimidinyl-4-1]-benzenesulfonamide are added to a solution of 20 g (178 mmoles) of potassium tert-butylate in 300 ml of ethylene glycol, kept in an inert atmosphere (nitrogen). Once the addition is complete, the suspension is heated to 110° C. and maintained for 24 hours. During the reaction, a complete solution is obtained. Once the reaction is complete, the solution is cooled to 90° C. and diluted with 300 ml of water. The solution is cooled to 15° C. and the product is left to crystallise for 5 hours. The suspension is filtered. 24 g in wet form equal to 19 g in dry form (32 mmoles) are obtained; yield 85%.

The reactions of the Examples 2, 5 and 6 resulted in a raw product with comparable purity; in particular, the "OH derivative" impurity (formula given below) was always <1.0%.

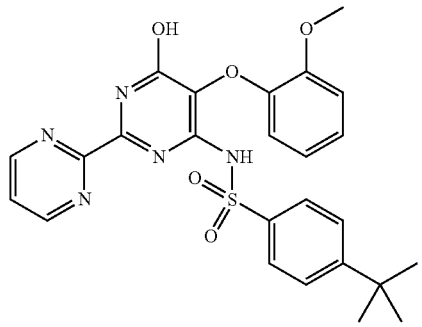

OH derivative impurity

COMPARATIVE EXAMPLES

In the following comparative examples the process of the invention is reproduced using hydroxides as the base.

Comparative Example A

Preparation of the Compound of Formula (III) with Potassium Hydroxide 95%

20 g (38 mmoles) of 4-tert-butyl-N-[6-(2-hydroxy-ethoxy)-5-(2-methoxy-phenoxy)-[2,2']bipyrimidinyl-4-yl]-benzenesulfonamide are added to a solution of 11 g (186 mmoles) of potassium hydroxide 95% in 300 ml of ethylene glycol, kept in an inert atmosphere (nitrogen). Once the addition is complete, the suspension is heated to 110° C. and maintained for 24 hours.

A sample is taken for TLC: the OH derivative impurity is evaluated at approximately 10%. It was considered not expedient to proceed with processing of the reaction product.

Comparative Example B

Preparation of the Compound of Formula (III) with Potassium Hydroxide 99%

20 g (38 mmoles) of 4-tert-butyl-N-[6-(2-hydroxy-ethoxy)-5-(2-methoxy-phenoxy)-[2,2']bipyrimidinyl-4-yl]-benzenesulfonamide are added to a solution of 7.6 g (190 mmoles) of sodium hydroxide 99% in 300 ml of ethylene glycol, kept in an inert atmosphere (nitrogen). Once the addition is complete, the suspension is heated to 110° C. and maintained for 24 hours.

A sample is taken for TLC: the OH derivative impurity is evaluated at approximately 10%. It was considered not expedient to proceed with processing of the reaction product.

The invention claimed is:

1. Process for the preparation of bosentan or a potassium salt of bosentan
    which comprises reacting [4-tert-butyl-N-[6-chloro-5-(2-methoxy-phenoxy)-[2,2']bipyrimidinyl-4-yl]-benzene-sulfonamide of formula (II)

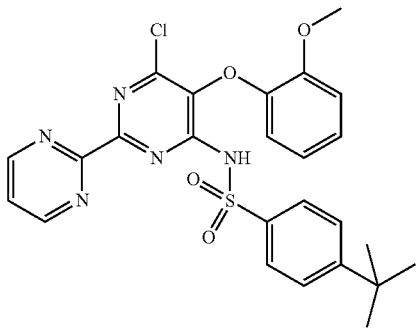

(II)

with ethylene glycol, in the presence of a base which is potassium phosphate tribasic ($K_3PO_4$)
    wherein the reaction is carried out in an inert atmosphere;
    wherein the reaction is carried out at a temperature between 90° C. and 120° C.;
    wherein ethylene glycol is used as solvent.

2. The process according to claim 1, wherein the reaction is carried out at a temperature of about 110° C.

3. The process according to claim 1, wherein the potassium salt of bosentan is purified by crystallization in ethylene glycol in the presence of a base selected from potassium phosphate tribasic ($K_3PO_4$) and potassium carbonate ($K_2CO_3$).

4. The process according to claim 1, wherein the potassium salt of bosentan is converted into bosentan or into bosentan monohydrate.

5. The process according to claim 4, wherein the potassium salt of bosentan is converted into bosentan monohydrate by reaction with an acid in the presence of water.

6. The process according to claim 5, wherein said acid is hydrochloric acid.

7. The process according to claim 6, wherein bosentan monohydrate is crystallized in ethanol and water.

* * * * *